United States Patent [19]

Miller

[11] 4,110,419
[45] Aug. 29, 1978

[54] HIGH-VOLUME DISPOSABLE AND SEMI-DISPOSABLE CARTRIDGE HUMIDIFIER WITH SELF-CONTAINED CARTRIDGE STERILIZING MEANS, AND RELATED METHOD

[75] Inventor: Kenneth G. Miller, Elk Grove Village, Ill.

[73] Assignee: Respiratory Care, Inc., Arlington Heights, Ill.

[21] Appl. No.: 826,119

[22] Filed: Aug. 19, 1977

Related U.S. Application Data

[63] Continuation of Ser. No. 569,490, Apr. 18, 1975, abandoned.

[51] Int. Cl.$^2$ .................................... A61M 15/00
[52] U.S. Cl. ................................ 261/142; 128/186; 128/192; 219/275; 219/535; 261/104; 261/DIG. 65
[58] Field of Search ............... 261/142, 104, 101, 102, 261/DIG. 65, 128–131, 141; 128/186, 212, 192–194, 188; 219/275, 535

[56] References Cited

U.S. PATENT DOCUMENTS

| 1,267,761 | 5/1918 | Goodfellow | 128/192 |
|---|---|---|---|
| 2,206,688 | 7/1940 | Bloomheart | 128/188 |
| 3,284,613 | 11/1966 | Gettelman et al. | 219/535 |
| 3,353,536 | 11/1967 | Bird et al. | 261/DIG. 65 |
| 3,534,732 | 10/1970 | Bickford | 128/188 |
| 3,912,907 | 10/1975 | Lodi | 219/535 |

FOREIGN PATENT DOCUMENTS

187,947 10/1966 U.S.S.R. .................................... 128/188

Primary Examiner—Frank W. Lutter
Assistant Examiner—Gregory N. Clements
Attorney, Agent, or Firm—Eric P. Schellin

[57] ABSTRACT

A cartridge-type humidifier apparatus embodying a separate heater module with a cylindrical opening for replaceably receiving therein disposable cylindrical humidifier cartridge modules. Certain upgraded embodiments of the cartridge modules are sterilizable and reusable several times before being disposed of, or portions thereof recycled. The cartridge modules each have a tubular metal main body adapted for a sliding fit within a complementary tubular walled heater. The metal tubular body has rigid plastic top and bottom end portions. The plastic top end portion is a cap with a center axial gas inlet tube, and a separate transverse gas delivery pipe, the cap forming a closed air space over a pool of humidifying liquid. Each cartridge includes an absorption column preferably of the cylindrical tube form which is adapted to lay closely adjacent and draw water up along the cartridge's cylindrical metal body wall which serves the evaporating surface when heated by the heater modules. The gas to be humidified is dispersed within a hollow chamber formed between the gas inlet pipe projecting concentrically into the cartridge, and the radially spaced wall of the main cartridge body and absorption column. The inlet tube always terminates above the water. The water may be introduced into the lower end portion by way of conduits or other communication means.

4 Claims, 8 Drawing Figures

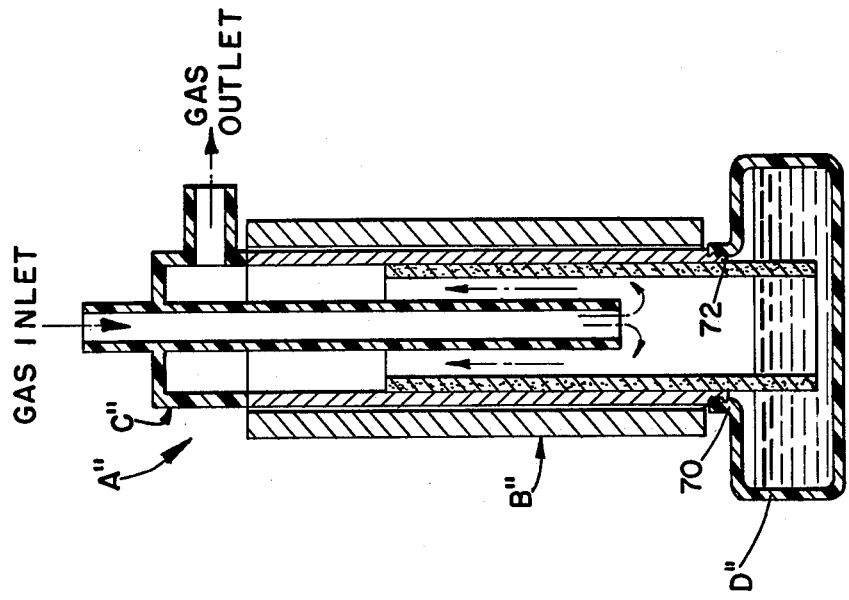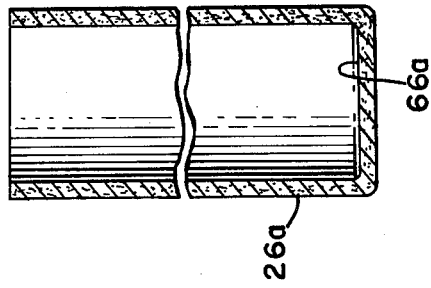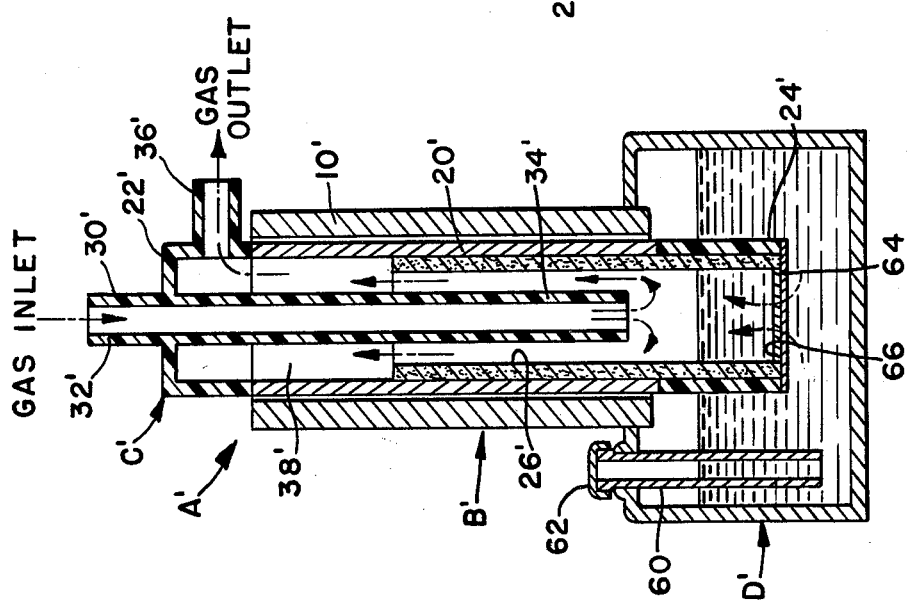

HIGH-VOLUME DISPOSABLE AND SEMI-DISPOSABLE CARTRIDGE HUMIDIFIER WITH SELF-CONTAINED CARTRIDGE STERILIZING MEANS, AND RELATED METHOD

This is a continuation of application Ser. No. 569,490, filed Apr. 18, 1975, now abandoned.

BACKGROUND OF THE INVENTION

The present invention relates generally to humidifying means and more particularly to improved humidifying means embodying an externally heated, disposable or semi-disposable humidifier cartridge for use in respiratory inhalation therapy.

In such humidifying means, oxygen, air or other gases which are to be breathed by a patient being aided in his respiration, are preferably both heated and humidified under controlled conditions, including the need to use a sterile liquid for humidification. It is known that in many hospitals where inhalation therapy is practiced, the respirator and ventilator equipment often utilized is primarily of a reusable, sterilizable and heatable type, based generally upon the type which introduces bubbles of gas into a water reservoir.

Some such prior art units are often accompanied by some objectionable features which include: difficulty in sterilizing; inability to quickly heat up to the desired temperature range due to the relatively larger volume of water used; the relative arrangement and functional disposition of the components is such that objectionable back pressure evolves in the system; that it cannot be filled or refilled while the humidifying unit or apparatus is in operation; and, an inability to effectively use all of the sterile water or humidifying liquid which is placed into the reservoir thereof.

It is also known that heretofore disposable humidifier cannisters or cartridges encapsulating sterile liquid have been invented or marketed, which generally overcome any problems related to sterilizing of the liquid. However, those humidifying devices still are plagued with many of the same problems stated above, and often to a greater degree. That is, the bubble-type disposable humidifiers are even slower in heating up to the desired temperature range, and provide more objectionable back pressure. Moreover, they still cannot be filled while in operation, and are unable to use all of the sterile water placed in their reservoir. Still further prior art devices have embodied quite elaborate and sophisticated electronic controls which generally are non-immersible, for example, for purposes of sterilization.

It is a principal object of the present invention to provide improved humidifying apparatus which benefits from the sterility advantages of utilizing various forms of initially sterilized cartridged together with disposable cartridges of the encapsulated sterile liquid in most preferred forms, while basically eliminating the other stated disadvantages attendant some of the known prior art devices.

It is a further object to provide an improved humidifier of the aforementioned character which lends itself to a very effective self-contained steam-disinfecting or sterilizing system permitting limited reuse of certain of the contemplated cartridge modules herein.

Still another object is to provide an improved cartridge type humidifier, which by its nature heats only a relatively small quantity of water at any time, and which permits a very rapid reaction to a change in thermostatic or other control, thereby lending itself to electronic control of a temperature feedback nature to be described hereinafter, to facilitate continuous monitoring and self-compensating control of a preset temperature, attendant variations in room temperature, flow rate, etc.

A still further object is to provide up-graded variations of the cartridge modules which will lend themselves to autoclavable sterilization for reuse over several applications, whereby characterizing the cartridge modules as semi-disposable, and subject to sterilization by other than use in the self-contained unit hereof.

SUMMARY OF THE INVENTION

According to the basic concept, my improved humidifiers utilize improved disposable or semi-disposable cartridge modules. The cartridges comprise a special paper-like absorption column which is basically sheathed within a metal sleeve, and has non-metallic top and bottom end caps designed so as to allow the humidifying liquid, hereinafter called water, to enter via the bottom cap to the bottom of the special column, and to then direct the treatment gas or air flow through the center of the absorption column via entry through the top cap of a preferably concentrically disposed smaller diameter gas inlet tube, the latter of which terminates above the water level in the lower end of the cartridge. The improved disposable or semi-disposable cartridge and attached water supply are preferably heated by an externally disposed perferably tubular heater element. The specific details of the heater per se are not considered to be an inventive facet of the invention. In operation, the water from the associated sterile water reservoir is connected to enter a lower portion of the cartridge so as to leave an air space above the level of the water. The surrounding tubular heater generates heat which is transferred through the metallic wall portion of the cartridge, whose inner conducting surfaces form evaporating surfaces in the air space for transmitting water vapor to the gases entering and passing therethrough, having entered via the top cap as stated hereinabove.

Three improved embodiments have been evolved, utilizing the basic novelly improved cartridge, and which differ from one another primarily in the manner of introducing the water in a sterile manner into the associated humidifier cartridge. One embodiment uses the novelly improved cartridge having appropriate inlet and vent tubes, and which is adapted to use containers of pre-packaged sterile water as the humidifying liquid source.

A second form utilizes a generally permanent type water reservoir in conjunction with the tubular heater and into which is placed the lower end of a cartridge having a lower end cap provided with a water permeable bacteriostatic filter therein. Upon insertion of the cartridge and the attendant immersing of the lower filter end portion into the water reservoir, the only water which is thereby introduced into the cartridge is of a filtered or sterile character which serves to wet the special absorption column, the latter of which may be made from a roll of 3mm chromatography paper.

The third embodiment uses a cartridge of this type but which has no bottom, and which is insertable into a selectively attachable/detachable disposable container of preferably pre-sterilized liquid.

In each embodiment, the device is provided with the necessary tubes for respectively introducing the gas to be humidified, the humidifying liquid vent tubes, and for delivering the humidified gas to the patient at a predetermined temperature range to be described in more detail hereinafter. The present improved cartridge type humidifiers using the absorption column have been found to have the following advantages over known prior art bubble type humidifiers: Faster warm up; the cartridge provided is sterile and disposable; certain upgraded cartridges may be semi-disposable and capable of resterilization for several reuse applications; no back pressure in the system; absolutely quiet - no bubbling; substantially no water wasted; minimal or no hose condensation because humidified gas can be super heated above the saturation temperature, whereby the gas at remote patient end of the delivery hose, which is cooler, is saturated, when using pre-packaged aseptic water reservoir mounted in predeterminable position, water supply reservoir bottle can be replaced, or humidifier water can otherwise be injected into a filter-provided reservoir without splashing or spraying caused by rush of gas during cycling of related ventilator when attempting to refill while in operation and with humidifier unit in operation, such that aseptic fill and water level control is achievable and a sterile environment is maintained within the cartridge without need for pre-sterilized water; 200 ml. water can be injected into reservoir for short duration (4 hours); high output temperature (up to 110° F) with smaller physical size; required heater element surface temperature is substantially lower, for example, 180° F. vs. 330° F.; no abrupt temperature increase when flow rate is increased; no need for inlet tube bleed hole as in some prior units to transmit patient triggered inspiratory pressure drop with ventilator use; no plastic material distortion; both disposable or semi-disposable cartridges are potentially recyclable by return of aluminum metal sheath and/or plastic material end caps from the cartridge to allow factory replacement of the paper absorption element; cartridge is free to swivel within heater console or module, enabling outlet port or tube to be adjusted; the unit is not fragile, and not susceptible to shipping damage, with packaging thereof easier and cheaper.

The humidifier system hereof contemplates the utilization, in regard to the heater, of either a manually or automatically timed 30-minute temperature over-ride circuit, to be initiated by a switch. An audible and/or visual signal, such as a buzzer and a red light, would be provided in conjunction therewith. During the exemplary 30-minute period, the heater's temperature would be increased from its normal temperature of approximately 180° F. to approximately 240° F., thereby producing the steam within the wet cartridge. The system would further embody a feedback temperature sensor means such as a thermistor located near the patient, thereby allowing continuous monitoring and control of the normally set temperature, and self-compensating for changes in room temperature, flow rate, etc. The system might be considered similar in the temperature feedback aspect to that of assignees co-pending application Ser. No. 461,753.

These various forms of the invention will be described in more detail, having reference to the accompanying illustrative drawings.

BRIEF DESCRIPTION OF THE DRAWINGS

FIG. 3 is a cross-sectional view similar to FIG. 2 and showing in semi-schematic form another embodiment of the invention hereof;

FIG. 4 is a further cross-sectional view, similar to FIGS. 2 and 3, and showing a third embodiment of the invention;

FIG. 5 is a fragmentary detail of a modified absorption column;

DETAILED DESCRIPTION OF PREFERRED EMBODIMENT

Figure 1:
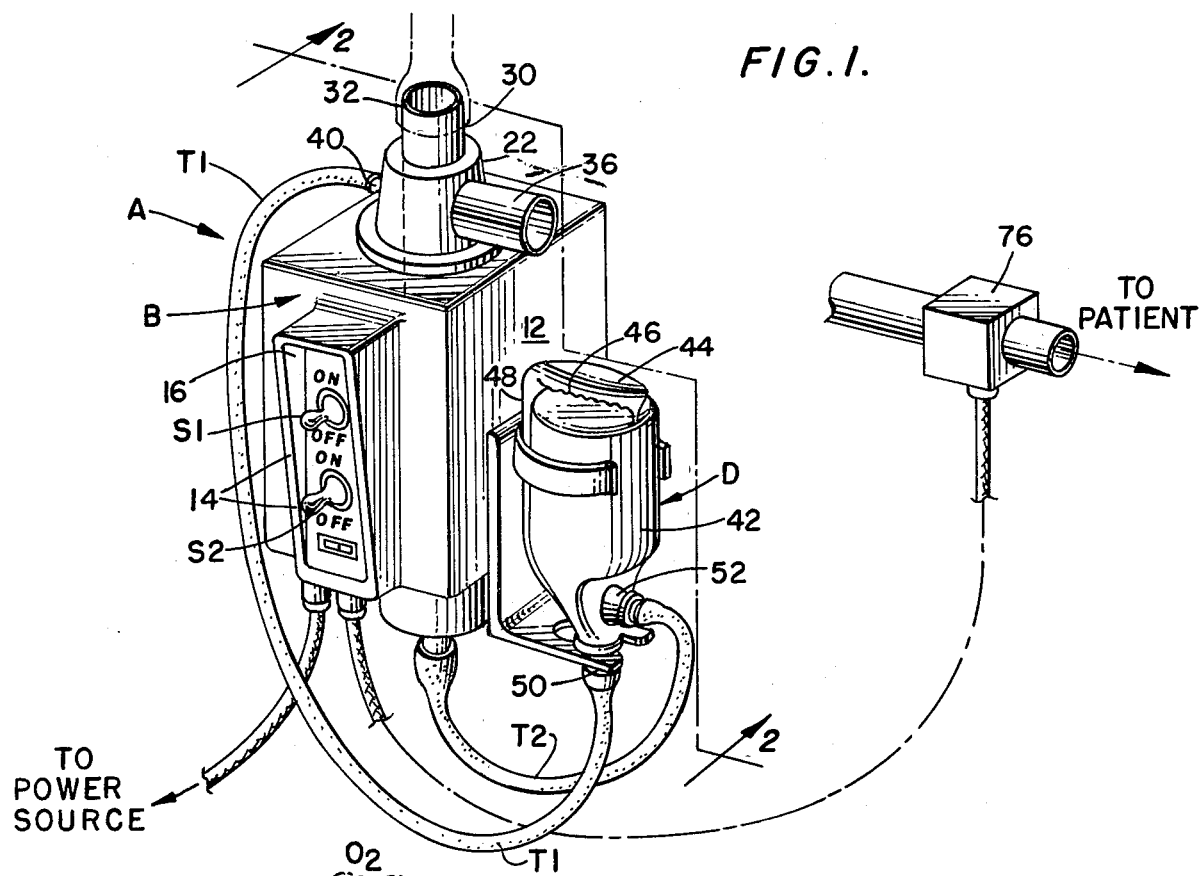
FIG. 1 is a perspective view of an assembled humidifying apparatus according to one form of the invention.
Figure 2:
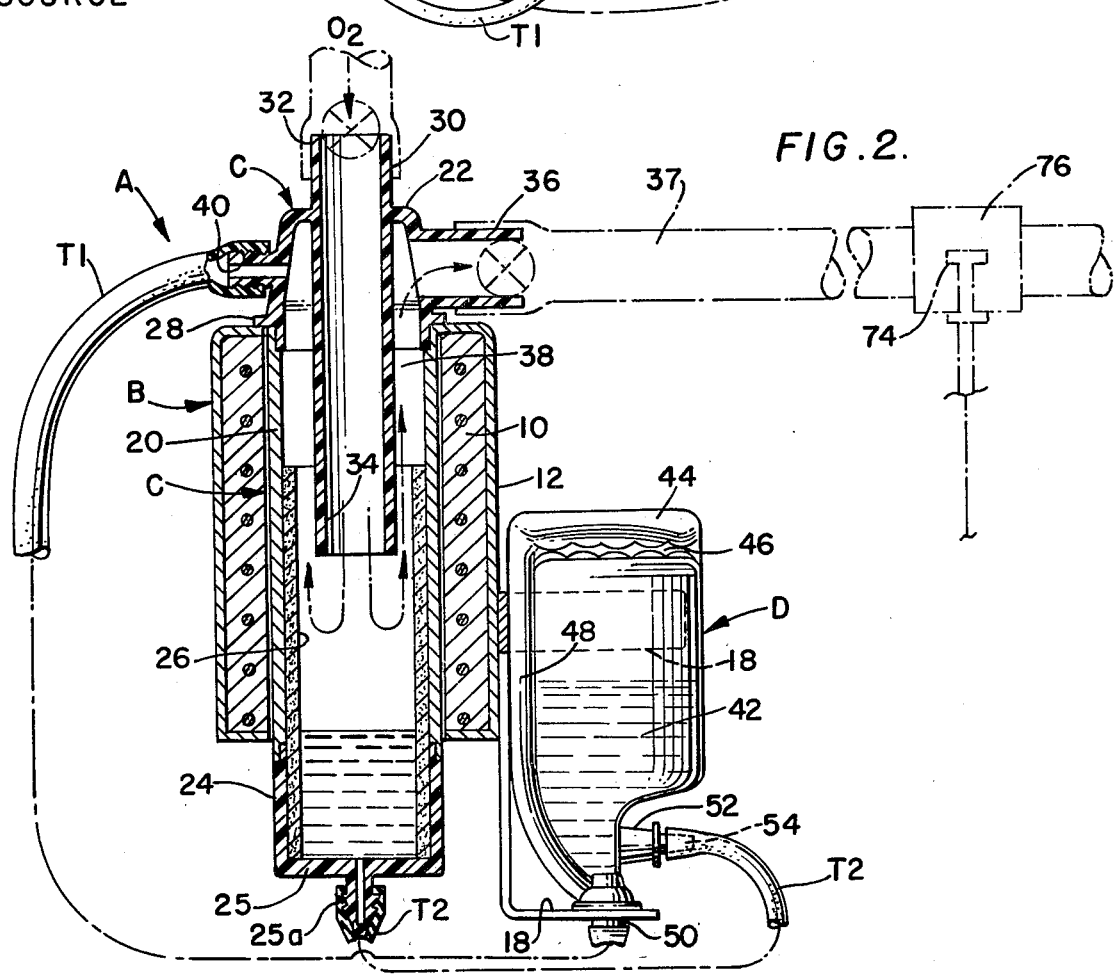
FIG. 2 is a vertical cross-sectional detail view of the apparatus of FIG. 1, as viewed substantially on line 2—2 thereof.

Reference is made first to FIGS. 1 and 2 of the drawings, wherein an illustrative humidifier assembly is generally designated A, and comprises a combined heater and cartridge supporting module B, disposable or semi-disposable humidifier cartridge module C, for use with a disposable water reservoir module D.

Figure 6:
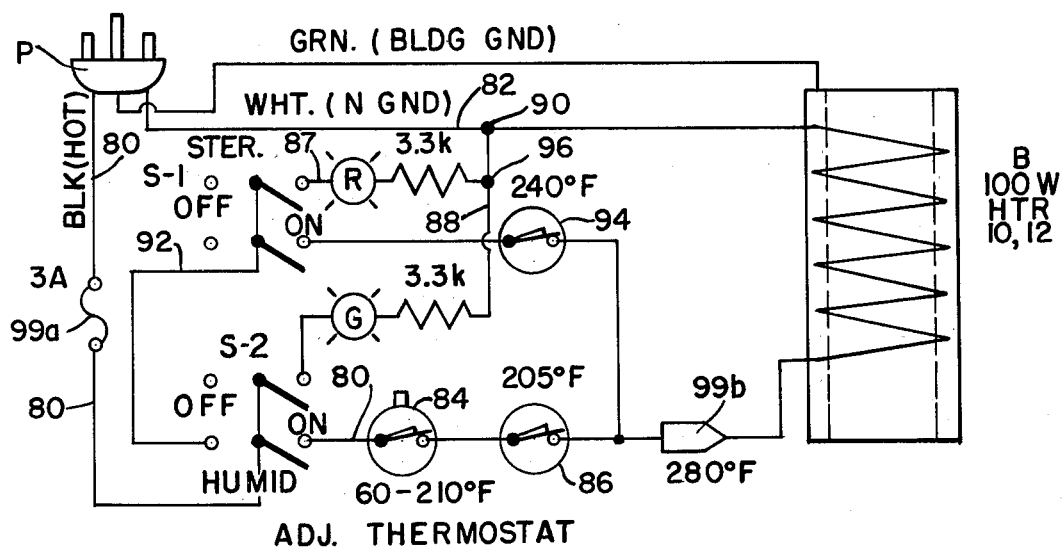
FIG. 6 is an exemplary electrical schematic showing the selective preliminary sterilizing and normal humidifying circuitry.

The combined heater and cartridge-supporting module B may comprise any suitable jacket type heater such as an open end metal cylindrical sleeve 10 provided with a suitable resistance heating element 11, and a suitable thermostatic control of any well known type, shown only in the schematic of FIG. 6, to be described hereinafter. Sleeve 10 may be fabricated from brass tubing or the like, having an exemplary diameter of 2⅛ inches, a 0.051 wall thickness and a length range of approximately 5–7 inches or whatever dimensions may be warranted to meet certain output conditions. A 100-watt band type heater element in conjunction with the sleeve 10 was found to perform very well, and was connected in a conventionally known manner with a single bi-metallic thermostat which may be suitably set to 185° F., to regulate the temperature of the humidified gases passing through the apparatus.

Sleeve 10 is encased in the illustrated open-ended manner within a preferably insulated housing shell 12 of any suitable rigid material. The thermostat and related heater controls 14 (FIG. 1) may be housed within a lateral projection 16 on the housing 12. Any suitable form of switch may be used therein to initially energize the heating element. Housing shell 12 is further preferably provided with suitable support means (not shown) by which the shell/module B may be suitably suspended or otherwise supported for inhalation therapy use together with a preferred form of the cartridge to be described.

Additionally, shell 12 is preferably provided with bracket means 18 to support therewith a suitable prepared liquid supply module D in predetermined relationship to be further explained hereinafter. One type of such liquid supply module D with which the system hereof is designed to work, is the aseptically prefilled liquid reservoirs known as AQUAPAK ®, preferably the AQUAPAK 500 (500 ml.) marketed by Respiratory Care, Inc. of Arlington Heights, Ill. 60004. Details of exemplary modules D will be described hereinafter and/or may be obtained to a greater degree by reference to U.S. Pat. Nos. 3,807,713 and 3,325,860. The manner of encasing the heater sleeve 10 in the stated open-ended manner is such that the cylindrical cartridge module C, now to be described, can be readily inserted into the open top end thereof, with access provided via the open bottom end for operative connection with liquid reservoir means to be described in more detail hereinafter.

A practical form of a disposable or semi-disposable type humidifier cartridge module C, which has performed well, may have a cylindrical body comprised preferably of a metallic main body sleeve member 20, which is provided with preferably a non-metallic top body and end cap 22 and similar non-metallic bottom end cap or liquid-contacting portion 24. The diameter of the assembled cartridge is such as to have a sliding fit within the heater sleeve 10. An exemplary form of body sleeve 20 may be fabricated of 2 inch diameter aluminum tubing of appropriate length corresponding generally to the approximate proportions of the illustrative drawings. The end caps 22 and 24 may be fabricated of any suitable rigid type plastic material or the like as polycarbonate material which will not be adversely effected by the heater sleeve 10.

Cartridge module C further comprises an absorption column 26 which in one preferred mode is of a hollow cylindrical form fabricated of an absorbent blotter-like paper material, for example, 3mm chromatography paper. Absorption column 26 is of a size to lay closely against the inside diameter of the cartridge body, and functions to draw humidifying liquid up into the hollow center portion of the cartridge for evaporization therein to moisture-laden gas directed therethrough in a manner to be better described. The vertical length of the absorption column 26 may be greater than shown and may extend substantially the full length of the heater sleeve 10, if desired, for some embodiments.

Upper end cap 22 has its open mouth portion unitarily joined in any suitable manner to the upper open end of intermediate body sleeve 20, and is preferably provided with positioning means such as radial lugs or a flange 28 for limiting the insertion of the cartridge into the heater sleeve 10 in accordance with predetermined limits. Cap 22 is unitarily provided with an axially centered gas inlet tube 30 having an upwardly projecting outer end 32 adapted to be connected with a source of air or oxygen supplemented air, and the like, to be humidified. The tube 30 is of a length so that its inner end 34 projects a substantial distance down into and preferably concentrically relative to the cartridge body sleeve 20, but terminates above the level of the water which is either introduced into the bottom portion of the cartridge, or into which the lower end of the cartridge C is immersed, depending upon the embodiment.

Cap 22 is further provided with a gas delivery port and connection pipe 36 extending transversely of the axis of the cartridge. Pipe 36 inwardly communicates with the inner radial space 38 defined between the gas inlet tube 30 and body sleeve 20, and operatively with the lower end of said gas inlet tube 30. A flexible tube 37, shown fragmentarily in broken outline, is connectable with the external end of the output pipe 36 and is adapted to deliver the humidified gas to the patient.

Additionally, in cap 22 there is another transverse pipe connection 40 of relatively smaller diameter than pipe 26, which is adapted to communicate by flexible vent tube T1 with a venting outlet 50 of the particular water reservoir module D and with the aforesaid interior space 38.

It is apparent that this conduit tube T1 provides for venting of the reservoir D during delivery of liquid therefrom via flexible conduit tube T2 into the bottom of the cartridge C, while maintaining an aseptic assembly by use of sterile tubing and cartridge modules.

The lower end portion or cap 24 of cartridge is provided with liquid holdimg means such as an apertured and nippled transverse end wall 25, which may be made integrally therewith, or may have a slip fit assembly with the open cylindrical end of portion 24. The nipple 25a thereof is adapted to be connected with one end of the flexible delivery tube T2.

The liquid or water reservoir module means in this embodiment of FIGS. 1 and 2 is preferably one of the aforesaid sealed AQUAPAK units placed in an inverted condition, which unit is a disposable sealed plastic container of aspetic water. The container comprises a principal chamber 42 and a secondary foot chamber 44 which are communicatively separated from one another by an interrupted pinched-together wall portion 46. In the illustrated inverted disposition of the AQUAPAK D, the foot portion 44 became a top portion. The container D further has along one vertical side an integrally formed vertical conduit 48 which is fluidly connected at one end with the said foot portion described more fully in U.S. Pat. No. 3,807,713. Conduit 48 at its other end terminates in a neck-like outlet 50 provided with a breachable seal and adapted to be connected with an end of the flexible conduit tube T1. The container integrally embodies another neck-like outlet 52 connecting directly with principal chamber 42 and terminating in a breachable sealed nipple 54 adapted to be connected with the second flexible conduit T2. In the manner of use as depicted in FIGS. 1 and 2, the sealed AQUAPAK is invertedly disposed so that essentially all of the liquid is confined in the principal chamber 42, from which it is adapted to flow out of outlet 52 via tube T2 and into the lower end of the cartridge via nipple 25a. The liquid reservoir module D is disposed by bracket means 18 so as to preferably have its liquid delivery outlet 52 above or substantially coplanar with the bottom transverse wall 25 of the cartridge, in order to assure maximum use of the liquid during operative use of the humidifier apparatus.

Preferably both caps 22 and 24 are of a viewable clear, relatively rigid plastic or plastic-like material. Lower plastic portion 24 of the cartridge module C is of a length or height corresponding preferably to the maximum height at which the humidifying liquid is desired to enter into that portion of the cartridge. By this arrangement, the desired output temperature of the humidified gas is better maintained, by avoiding heat sink loss attributable to having the lower portion of the metal intermediate sleeve 20 immersed in the constantly replenishing water.

The manner of adjoining the plastic end caps 22 and 24 to the respective ends of the cylindrical sleeve 20, may be as shown in FIG. 2. That is, the mating ends may be complementarily grooved or shouldered so that the I.D. of the metal body sleeve 20 and that of the cap 24 are essentially the same, thereby providing a continuous smooth surface against which the O.D. of the absorption column 26 should engage.

Figure 8:
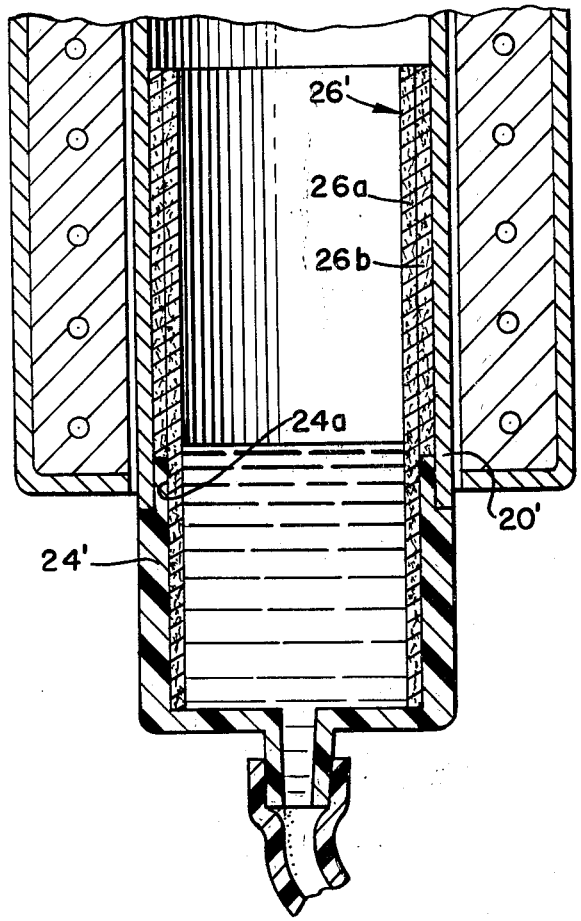
FIG. 8 is an enlarged fragmentary detail of the lower end cap of a modified cartridge embodiment.

Reference is temporarily made to the modification shown in FIG. 8, wherein the lower end of the sleeve 20' is not shouldered or recessed to complementarily receive the annular shoulder or flange 24a of lower cap 24'. In such an instance, where the I.D. s of the sleeve 20' and cap 24' are not coextensive, the absorption cylinder or column 26' is provided with a compensating shouldered end to assure substantially flush contact of the column's O.D. with the I.D. of sleeve 20'. A further contemplated form of the column would be to utilize concentrically disposed and interengaging sleeve-forming layers 26a and 26b of different end lengths as shown in said FIG. 8.

Figure 7:
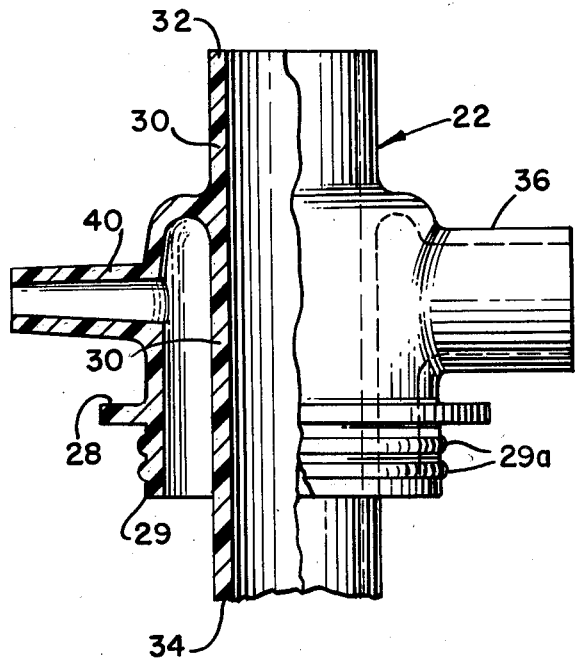
FIG. 7 is a fragmentary detail partially in elevation and partially in cross-section of the upper cap of the cartridge.

In the enlarged representation of FIG. 7 of an upper end cap 22, flange 28 is preferably provided with a depending skirt portion 29 provided with annular sealing ribs 29a for assuring a fluid-tight fit when assembled within the body sleeve 20. A similar construction may be used for the bottom cap 24.

Reference will now be made to the electrical schematic of FIG. 6, which shows selectively actuable circuitry to initiate either a preliminary sterilizing cycle, the purpose to be described in more detail hereinafter, or the desired humidifying cycle.

Switches S-1 and S-2 represent double pole double throw switches in the circuitry for selecting the override sterilizing circuit, or alternately the humidifying circuit respectively. The source of electricity is feedable through a conventional three wire convenience plug P. Conductor wires 80 and 82 are connected to the heater B. Switch S-2 is interposed in the conductor 80 along with an adjustable thermostat 84 and a preset fixed thermostat 86 connected in series as shown. One set of the double switch poles, designating the "on" side, connect with the continuing portion of the conductor wire 80, and an auxiliary signal-generating conductor wire 88 leading to and connecting with conductor wire 82 at junction 90. A green signal light G is interposed in the line 88 to signify when the normal humidifying circuitry is in operation. The latter is when the switch S-2 is closed to the "on" position and switch S-1 is in the "off" position.

When it is desired to override the humidifying circuit for use of the sterilizing circuit, switch S-2 is placed in the "off" condition, and S-1 is placed in the "on" condition. By this arrangement conductor wire 80 leading from the plug is connected with auxiliary conductor wire 92 leading into the switch S-1. The lowermost "on" pole of switch S-1 enables the circuit to be connected to the heater through another fixed thermostat 94 set to preferably about 240° F., so as to cause the heater to generate sterilizing steam within the wet cartridge module, as will be described hereinafter.

The other side of the "on" position of double pole switch S-1 connects via wire 87 into wire 88 at junction point 96 beyond the green signal light G. A red signal light R is also interposed serially in line 87 as shown, to signify when the sterilizing circuitry is in operation.

Fuses such as 99a in line 80 leading from plug P, and 99b in line 80 just preceding the heater B, may be used as safety measures.

A test of one prototype of this first-described embodiment was conducted, wherein the cartridge was made from a 7 inch length of 2 inch diameter aluminum tubing, having 0.035 inch wall thickness. The end caps were of acrylic plastic, and the absorption column was a roll of 3mm. chromatography paper. The heater portion was made from a 7 inch length of 2⅛ inch diameter brass tubing having 0.051 inch wall thickness, with a 100-watt band heater element. The single bi-metallic thermostat used therewith was set to 185° F. This humidifier was operated at a room temperature of 71° F. for a period of 3 hours with a Puritan-Bennett model MA-1 ventilator (not shown) supplying 1000 ml. volume at 12 cycles per minute, 50-liters-per-minute peak flow. The result achieved was a saturated output (100% R.H.) at 106° F., which was a stable output temperature measured at the end of a 3-foot 22mm. rubber hose. This temperature was reached in less than 10 minutes.

Tests were made using the same type cartridge but made with an aluminum main body tube of only 5 inches long, and it was found that the output was essentially the same, thereby indicative of potential substantial cost savings in production of the units.

OPERATION OF PREFERRED EMBODIMENT

While it is believed that the operation of this embodiment is fully apparent, a quick review thereof will be made. Water from the reservoir D flows via outlet 52, and tube T2 into the lower end portion of the cartridge module C. Cartridge C is heated, and oxygen or some oxygen supplement gas to be humidified is introduced via inlet pipe 30 where it is circulated over the water and in moisture-pick-up relation to the gas-exposed evaporating surfaces of the heated absorption column 26, and of heater sleeve 20. Moisture is thereby picked up in vapor form with the gas flow, indicated by the flow arrows in FIG. 2, to a predetermined degree of saturation, which is maintained throughout the output delivery within tube 37 to the patient. It is preferably that heat and the degree of saturation to be substantially 100% and such that condensation in the output tube 37 is precluded, or otherwise kept to a minimum.

DESCRIPTION OF MODIFIED EMBODIMENTS

Referring next to FIG. 3, a modified humidifier assembly A' is depicted in semi-schematic form, with certain of the component parts corresponding to their counterparts in FIG. 2 being designated by primed reference characters. Therefore, not all components need to be redescribed, but generally will bear the corresponding reference numbers, the description being apparent from the foregoing disclosure.

A generally permanent liquid reservoir container D' is provided in association with the heater module B' to serve as the liquid holding means thereof. Reservoir container D' includes a filler tube 60 which preferably extends close to the bottom thereof so that liquid can be injected therein without splashing. Tube 60 is provided with a removable cap 62, preferably of the vented type.

A modified cartridge module C' is utilized, and differs from that of FIG. 2 primarily by the open lower end cap 24' which has sealingly affixed transversely thereacross a liquid permeable bacteriostatic filter element 64. Use of the filter 64 enables introduction into the reservoir of non-sterilized liquid. While assuring that only aseptic filtered water wets the absorption column 26', used to humidify the inflowing gas. An example of one suitable filter element is a 47mm. Millipore ® filter (0.45 M porosity) made by the Millipore Corporation of Massachusetts.

In one series of satisfactory tests, the cartridge was placed into the heater cylinder with the lower end immersed 5cm. under the water level. The unit was run at a room temperature of 71° F. for 4 hours with a Puritan-Bennett module volume MA-1 ventilator supplying 1000 ml. at 12 cpm. The results were favorable, with the rate of water inflow through the filter being such as to fully humidify the supplied gas at a satisfactory delivery temperature. To prevent unnecessary heat sink effect, the lower end portion 24' of the cartridge which is wetted or immersible also should be made from the plastic material, rather than the metal of main body sleeve 20'. No vent pipe equivalent to pipe 40 in the top cap is needed in this embodiment.

Because of the inherent structural weakness of filter unit 64, it has been found advisable on occasion to strengthen it by use of a supplemental absorbent disc 66, which simultaneously functions to preclude forcing of the liquid back out of the lower end of the tube during operational intermittent pressurization.

In this respect, the absorption column 26' can be further modified, as shown in FIG. 5, so that the open column portion 26a and the supplemental disc portion 66a are made integrally as a closed end tube or cup.

Reference is next made to the embodiment depicted in FIG. 4, whose basic structure and function remains the same as the embodiments of FIGS. 2 and 3. The component parts corresponding to previously described parts will be designated with the same basic reference characters but which are double primed.

Assembly A" basically differs from that of FIG. 3 by the use of a different form of liquid holding means such as a replaceable and disposable sterile water reservoir D", from that shown in FIG. 2.

The reservoir D", may be a plastic container formed with a neck 70 which may be provided with either male or female threads 72. Threads 72 are adapted to receive complementary threads of a sterile cap (not shown) unless provided with a breachable seal, prior to assembly with the heater and cartridge modules B" and C", collectively. When ready for use the cap (not shown) is removed and the threads 72 of neck 70 are mated with complementary threads preferably on the lower end of the cartridge module C", as shown. The operation remains essentially the same as that in FIG. 3, except that by using containers with pre-sterilized water there is no need for the filter element 64, which is not shown in FIG. 4.

In a further contemplated embodiment directed to a self-contained steam-disinfecting or sterilizing system unique to the industry, the invention would embody either a manually or automatically timed temperature override heating circuit. For example, the sterilizing circuit could be initiated by the switch S-1 (FIG. 1) for an exemplary period of 30 minutes, during which it would cause the heater's temperature to be increased from the normal of approximately 180° F. to approximately 240° F., thereby producing steam in the wet cartridge to sterilize or disinfect the unit. A conventional visual signal, such as a colored, preferably red, light R, may be further embodied within the housing unit B to indicate when the override circuit was in operation. An audible signal, (not shown) preferably would be selectively embodied also to indicate the end of the 30 minute cycle, when the sterilizing period was completed.

Such a system would preferably have a form generally like that depicted in FIGS. 1 and 2. During the sterilizing cycle the upper ports of the humidifier unit would be effectively closed, as shown by valves interposed in the various lines, thereby forcing the steam produced to fill the cartridge and thence forced out of the bottom outlet 25a, whose flexible conduit or tube T2 had been previously disconnected. At the end of the sterilization period, the override heating circuit would become disconnected, the conduit or tube T2 would be reconnected when using the form of FIG. 2, and the regular heating circuitry for heating the humidified oxygen would be placed in operation. Test results have proven the system and process to be very effective.

Additionally, by virtue of the unit's design, wherein the humidifier heats a relatively small quantity of water at any given time, a very rapid reaction to a change of thermostatic setting or other control is achievable. Therefore, this lends the unit to electrical or electronic control of a temperature feedback nature. For example, a feedback thermistor type sensor, 74 or the like, could be housed within an adaptor 76 adapted to be connected in the delivery tube 37 near the patient site, as shown in FIG. 1. By utilization thereof, generally in the manner disclosed in assignee's co-pending application Ser. No. 461,753, which except for the different heater details thereof, may be incorporated herein by reference, the temperature of the humidified oxygen stream flowing to the patient can be sensed, monitored and controlled in a known manner. This would control or maintain a preset temperature and would be self-compensating for changes in the room temperature, flow rate, etc., similar to that described in the aforementioned application Ser. No. 461,753.

It is further contemplated that the cartridge modules or units may be fabricated in further upgraded forms utilizing a plastic material of a character adaptable to withstand autoclavable sterilization when desired.

CONCLUSION

In each of the foregoing embodiments, the high level of the water in the liquid reservoirs is always below the end of the gas inlet tube. The use of the aforementioned thermostatic control in association with preferably electrical-resistance type heat generating means of the heater assures that the liquid and/or humidifier gas will not be overheated beyond predeterminable limits.

Concluding comments concerning certain advantages over the bubble-type humidifiers, emphasize the advantage of a much faster response to temperature adjustment because of the lesser quantity of water being heated in this cartridge type humidifier. This advantage is also apparent whenever the flow rate is changed. In bubble-type humidifiers, the temperature output has been found to increase abruptly and temporarily when the flow is increased, then the temperature drops off. The higher temperatures reached during this peak can be significantly higher than desirable.

The present cartridge-type humidifier invention displays no such temperature peaks, thereby providing a significant advantage and greater safety to the patient.

From the foregoing disclosure, it is apparent that patentably novel cartridge-type humidifier combinations have been evolved which satisfy the objects and disadvantages set forth in the beginning and throughout the specification.

Other variations and modifications to the disclosed humidifiers, for example, heater and humidifying cartridge modules of a uniform type of material, or of tapering or other non-uniform cross-section, and others, may suggest themselves to those skilled in the art without departing from the inventive spirit and scope as defined in the appended claims.

What is claimed is:

1. Cartridge type humidifying apparatus for use with a heating means for humidifying and heating a breathable gas to be inhaled by a patient undergoing inhalation thereapy, said apparatus comprising in combination:

(a) humidifier cartridge module means embodying a tubular cartridge main body portion with an inner peripheral wall;

(b) said humidifier cartridge module means also including an upper end portion with cap means attached to said main body;

(c) said humidifier cartridge module means including a lower end portion terminating in a transverse wall and adapted and constructed to retain a humidifying liquid, said transverse wall having liquid inlet means adapted to be fluidly connected via conduit means with a liquid outlet means of an external liquid source;

(d) said humidifier cartridge module means further comprising liquid absorption means including an open center generally tubular liquid-absorption column member with an inner peripheral face constituting an evaporating surface for humidifying liquid disposed generally contiguously and coextensive with a substantial part of said cartridge main body and said lower end portion adapted and constructed to be wetted directly by the humidifying liquid when liquid is in said lower end portion, and to convey by capillary action the liquid upwardly of said absorpting means and onto said evaporating surface;

(e) said upper end portion cap means of said humidifier cartridge module means of paragraph (b) together with a portion of said main body providing an air space above the humidifying liquid level in said lower end portion of said paragraph (c) when liquid is in said lower end portion;

(f) said cap means including a breathable gas inlet feed pipe for directing gas to be humidified into said module and terminating in said main body;

(g) said cap means further including an outwardly projecting humidified breathable gas outlet delivery pipe in fluid communication with said air space, said delivery pipe adapted to be connected with an output delivery tube leading to a patient.

2. The cartridge type humidifying apparatus of claim 1 wherein said cartridge main body is a predetermined length of tubular metal having good heat transfer characteristics, said lower end portion and said upper end portion with cap means are constructed of a non-metallic material having a lesser-transfer factor than said cartridge main body.

3. Apparatus for humidifying and heating a breathable gas to be inhaled by a patient undergoing inhalation therapy, said apparatus comprising in combination:

(a) heating module means for heating the gas to be delivered to a patient, comprising an upright generally tubular sleeve-type heat-conducting body;

(b) humidifier cartridge module means embodying a tubular cartridge main body portion with an inner peripheral wall and adapted and constructed to be axially received and disposed generally concentrically within and heated by said heating module means;

(c) said humidifier cartridge module means also including an upper end portion with cap means attached to said main body;

(d) said humidifier cartridge module means including a lower end portion terminating in a transverse wall and adapted and constructed to retain a humidifying liquid, said transverse wall having liquid inlet means adapted to be fluidly connected via conduit means with a liquid outlet means of an external liquid source;

(e) said humidifier cartridge module means further comprising liquid absorption means including an open center generally tubular liquid-absorption column member with an inner peripheral face constituting an evaporating surface for humidifying liquid disposed generally contiguously and coextensive with a substantial part of said cartridge main body and said lower end portion adapted and constructed to be wetted directly by the humidifying liquid when liquid is in said lower end portion and to convey by capillary action the liquid upwardly of said absorption means and onto said evaporating surface;

(f) said upper end portion cap means of said humidifier cartridge module means of paragraph (c) together with a portion of said main body providing an air space above the humidifying liquid level in said lower end portion of said paragraph (d) when liquid is in said lower end portion;

(g) said cap means including a breathable gas inlet feed pipe for directing gas to be humidified into said module and terminating in said main body;

(h) said cap means further including an outwardly projecting humidified breathable gas outlet delivery pipe in fluid communication with said air space, said delivery pipe adapted to be connected with an output delivery tube leading to a patient.

4. The apparatus of claim 3 wherein said cartridge main body is a predetermined length of tubular metal having good heat transfer characteristics, said lower end portion and said upper end portion with cap means are constructed of a non-metallic material having a lesser transfer factor than said cartridge main body.

* * * * *